United States Patent [19]
Schroeder et al.

[11] Patent Number: 5,591,395
[45] Date of Patent: Jan. 7, 1997

[54] METHOD OF DISINFECTING AIR

[75] Inventors: John A. Schroeder, Mount Pleasant; Armin L. Clobes, Wind Point; Arthur L. Hood, Mount Pleasant, all of Wis.

[73] Assignee: S. C. Johnson & Son, Inc., Racine, Wis.

[21] Appl. No.: 510,724

[22] Filed: Aug. 3, 1995

[51] Int. Cl.$^6$ .............................. A61L 9/02; A61L 9/14
[52] U.S. Cl. .................. 422/4; 422/28; 422/125
[58] Field of Search ...................... 422/1, 4, 28, 120, 422/123, 125

[56] References Cited

U.S. PATENT DOCUMENTS

| | | | |
|---|---|---|---|
| 2,597,195 | 5/1952 | Smith | 422/125 |
| 2,622,287 | 12/1952 | Eklund | 422/125 |
| 2,715,056 | 8/1955 | Wilson | 422/4 |
| 4,663,315 | 5/1987 | Hasegawa et al. | 424/76.3 |
| 4,745,705 | 5/1988 | Yamamoto et al. | 43/125 |
| 5,038,394 | 8/1991 | Hasegawa et al. | 392/395 |
| 5,095,647 | 3/1992 | Zobele et al. | 43/125 |
| 5,290,546 | 3/1994 | Hasegawa et al. | 424/76.2 |

OTHER PUBLICATIONS

U.S. Environmental Protection Agency article on "Efficacy Data and Labeling Requirements" dated Sep. 3, 1980.
The Journal of Experimental Medicine by Peyton Rous, Herbert S. Gasser & Rene Dubos The Rockefeller Institute for Medical Research 1947 (pp. 741–757).
The Journal of Experimental Medicine by Peyton Rous, Herbert S. Gasser & Rene Dubos The Rockefeller Institute for Medical Research 1947 (pp. 729–739).
Sterilization of Air by Certain Glycols Employed as Aerosols and Vapors by O. H. Robertson Trans. Assoc. Am. Physicians 1941 (pp. 353–358).
The Present Status of Glycol Vapors in Air Sterilization by Morton Hamburger, Jr., M.D., O. H. Robertson, M.D. and Theodore T. Puck, Ph.D. American Journal of Medical Science 1945 (pp. 162–166).
Testing Aerosol Products for Germicidal and Sanitizing Activity by L. S. Stuart and J. L. Friedl Proc. Chem. Spec. Mfg. Assn. 1955 (pp. 93–97).
Our Better Ordering and Preservation by Dr. Isaiah Bowman Science 1941 (pp. 212–215).
Glycol Vapors for Air Sanitation Soap and Sanitary Chemicals 1950 (pp. 122–124).
Epidemiologic Observations on the Use of Glycol Vapors for Air Sterilization by Edward Bigg, M.D., B. H. Jennings, M. E., and F. C. W. Olson American Journal of Public Health 1945 (pp. 788–798).
Sterilization of Air with Glycol Vapors by O. H. Robertson, M.D. Harvey Lect 1943 (pp. 227–254).
The Rate of Bacterial Action of Triethylene Glycol Vapor on Microorganisms Dispersed into the Air in Small Droplets by William Lester, Jr., O. H. Robertson, Theodore T. Puck, and Henry Wise American Journal of Hygiene 1949 (pp. 175–188).
The Journal of Experimental Medicine by Simon Flexner, M.D., Peyton Rous, M.D., and Herbert S. Gasser, M.D. The Rockefeller Institute for Medical Research 1943 (pp. 387–406).
Block, *Disinfection, Sterilization, & Preservation*, 1983, p. 970.

*Primary Examiner*—Robert J. Warden
*Assistant Examiner*—Theresa T. Snider

[57] ABSTRACT

A method of disinfecting the air and killing air borne bacteria, etc., by creating particles of disinfecting compounds using a heated wick is disclosed. More particularly, this invention relates to a method of generating particles of compounds which are known to kill air borne bacteria when these compounds are dispersed in the air in the fore of small particles by generating these particles using a wick which is indirectly heated at near the top. The compositions include glycols selected from the group consisting of propylene glycol, dipropylene glycol, triethylene glycol and mixtures thereof.

10 Claims, 1 Drawing Sheet

METHOD OF DISINFECTING AIR

The present invention relates to a method of disinfecting air and killing air borne bacteria, etc., by creating particles of disinfecting compounds using a heated wick. More particularly, this invention relates to a method of generating particles of compounds which are known to kill air borne bacteria when these compounds are dispersed in the air in the form of small particles by generating these particles using a wick which is indirectly heated at or near the top.

BACKGROUND ART

It has been long known to use indirect heating as a method of creating fumigating compounds for insecticide materials. An example of these types of compositions and methods are those disclosed in U.S. Pat. No 4,745,705, This patent discloses a method of delivering insecticides using a porous absorptive wick which is dipped into an insecticidal solution and indirectly heating the wick at the top to vaporize the absorbed solution into the atmosphere. There is no disclosure in this patent that the insecticides are dispersed into the air as particles.

In addition there have been a number of patents which disclose devices for delivering insecticides using a porous wick. These patents include U.S. Pat. No. 5,095,647, U.S. Pat. No 4,663,315, U.S. Pat. No. 5,038,394 and U.S. Pat. No. 5,290,546. None of these patents disclose that these devices can be used to generate particles of a disinfecting agent to the air.

Also, certain glycol compounds have been knows to provide some air sanitization when sprayed into the air. Generally these effective amounts have been found to be about 5% or more of active glycol. (US EPA document dated 03 Sep. 1980).

SUMMARY OF THE INVENTION

The present invention relates to a method of disinfecting air comprising immersing a portion of a porous wick in a liquid disinfecting composition and indirectly heating the top of said wick to generate particles of said active disinfecting agent into the air wherein at least 90% of the particles generated have a particle size of no greater than 5 microns.

BRIEF DESCRIPTION OF THE DRAWINGS

The attached drawing is a schematic view of a device to be used in the method of the present invention.

DETAILED DESCRIPTION OF THE INVENTION

Figure 1:
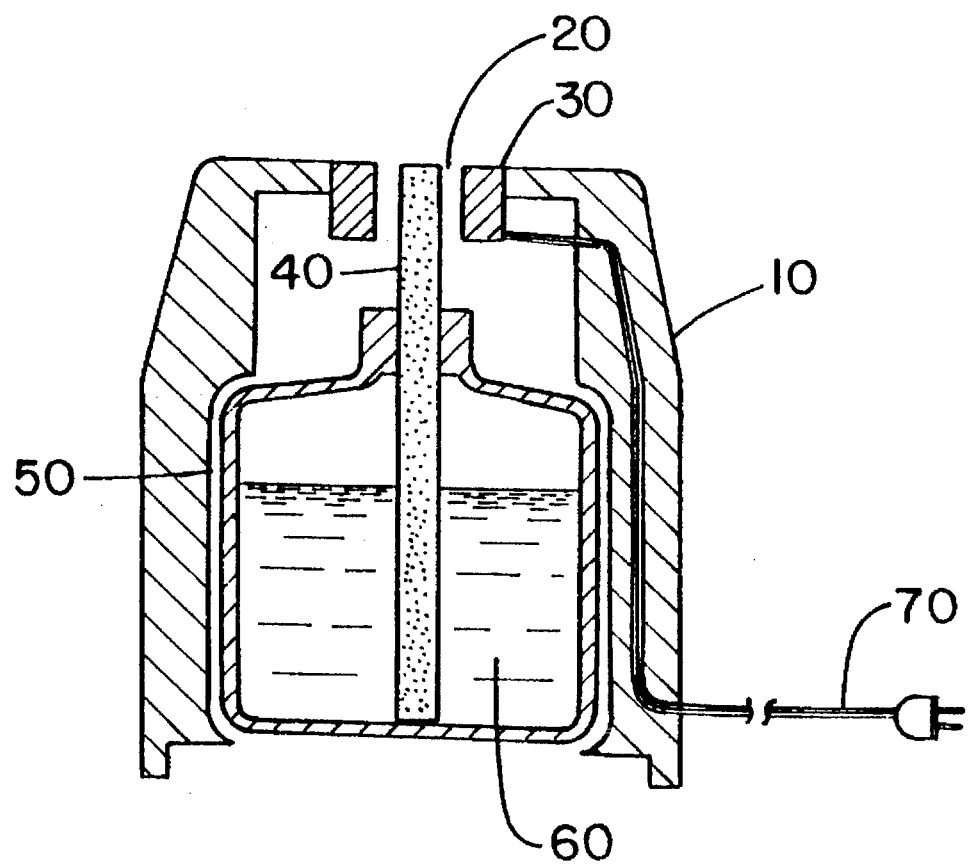

As noted above, it is well known that certain air disinfectant or air sanitizing agents must be present in the air in some form in order to be active. It is believed by applicants that the agents must be in the form of particles and/or attach themselves to particles already in the air, such as dust particles to be active. Therefore any such air disinfecting or sanitizing agent which can be dispensed in particulate form from a heated wick generator can be used in the method of the present invention. However, it is preferred that certain glycol compounds be used as these materials readily generate particles which form an aerosol suspension in the air at temperatures which can safely be used in a small consumer appliance. The preferred glycol materials are propylene glycol, dipropylene glycol, triethylene glycol, and mixtures thereof. Of these glycol materials, the most preferred compound is dipropylene glycol.

Since many of the air sanitizing active materials are water soluble the most preferred diluent for use in the method of the present invention is water. Other diluents, solvents and cosolvents can be used, however, it is believed that highly volatile hydrocarbon solvents decrease the efficacy of the method of the present invention and should in general be avoided. In addition, other volatile materials such as perfumes should also be avoided or used in small amounts, generally less than 15% of the total formulation. It is preferred that the formulations useful in the method of the present invention be essentially perfume free.

The particular concentration of the active material in the concentrate contained within the package suitable for use in the method of the present invention can range from as low as about 5% active to up to 100% active material. In this regard small amounts of a fragrancing agent or perfume can also be included without having an adverse effect on the air sanitizing effect of the active ingredient. Conversely, the amount of diluent present varies inversely with the amount of active from 0% diluent at 100% active material to about 95% diluent at about 5% active material. The preferred diluent materials are solvents for the active materials. For the glycols, the preferred diluent is water.

Turning now to the schematic drawing of the present invention, the present invention comprises an outer shell or container 10 which has contained within it at the top surface an opening 20. Located at the periphery of opening 20 is a heating element 30. This element can be any conventional heating element such as ring heaters, wire wound heaters or one or more PTC (positive temperature coefficient) heaters. The particular type of heating element is not critical to the present invention. So long as the heating element is capable of heating the top portion of wick 40 to a temperature in the range of from about 50° to about 120° C. Heating element 30 is connected by conductor 70 to a source of electric power. This can be a battery or home outlet.

Wick 40 can be made from any conventional material used for these type of wicks. Suitable materials include porous ceramic wicks and the like. Suitable wick materials are disclosed in U.S. Pat. No. 4,663,315, the disclosure of which is incorporated by reference. The preferred wick materials are ceramics, polyester, compressed wood, sintered polypropylene and polyethylene, and carbon fibers.

Wick 40 is placed in the opening of a container 50. Preferably wick 40 is placed in the opening of container 50 in a sealed manner such that the liquid air sanitizing material 60 within container 50 can not be easily removed. The means of sealing wick 40 in the opening of container 50 is conventional and forms no part of the present invention.

It was surprising that the above type of evaporator unit would generate particles of air sanitizers in a range where these known sanitizer materials would be active. It has been observed that the above units will generate particles such that over 90% of the particles have a particle size within the range of from about 0.16 to about 5 microns. Within this range of particle size the air sanitizer materials are very effective.

The present method will now be illustrated by the following examples which are for the purpose of illustration only and are not to be considered as limiting.

EXAMPLE 1

The following formulation was prepared:

| Components | Percent by Weight |
|---|---|
| Dipropylene glycol | 90 |
| Fragrance (TBA73299) | 10 |

45 grams of the above formulation was placed in a bottle with a ceramic wick having an average pore size of 0.7 micron. The bottle and wick combination was then placed in a electric heating unit that heats the top portion of the wick to a temperature of about 100° C. The unit was placed in a room with the temperature and humidity controlled to 22° C. and 40% RH. The room also was equipped with a Met One #200 Clean Room particle counter and a Mattson-Garvin 220 slit to agar impingement sampler, which measures the number of colonies of bacteria over time. After about 24 hours, an airborne bacteria, micrococcus lutens lysodiekticus, was introduced into the room. The total particle count as well as the relative particle sizes of the particles were measured. In addition the decline in the number of colonies over time was measured. A control room without any unit to generate particle also had the decline of the number of colonies of the bacteria measured. The above unit generated 6.39 million particles after a 24 hour period. The weight loss of the formula from the bottle over that time was 1.67 grams. In the following table, 10–15 refers to 10–15 minutes from introduction of the bacteria into the room. The bacteria colony counts were as follows:

| | 0–5 | 10–15 | 20–25 | 30–35 | 40–45 | 50–55 |
|---|---|---|---|---|---|---|
| Ex 1 | 1 | 0 | 0 | 0 | 0 | 0 |
| Control | 293 | 183 | 146 | 113 | 77 | 44 |

It is clear that the method reduces the amount of airborne bacteria after only a short period of time.

EXAMPLE 2

The procedure of Example 1 was repeated except that the following formulation was used

| Components | Percent by Weight |
|---|---|
| Triethylene glycol | 10 |
| Deionized Water | 90 |

The number of particles generated over a 24 hour period were 3.1 million and the weight loss was 0.98 grams. The following results were observed:

| | 0–5 | 10–15 | 20–25 | 30–35 | 40–45 | 50–55 |
|---|---|---|---|---|---|---|
| Ex 2 | 28 | 10 | 5 | 5 | 2 | 4 |
| Control | 322 | 256 | 161 | 134 | 110 | 77 |

Again there was a substantial reduction in the amount of airborne bacteria present.

Industrial Applicability

The method of the present invention is useful in reducing the amount of airborne bacteria present in an indoor environment. Since some bacteria are known to contribute to disease, the use of the method of the present invention may minimize the spread of certain infections.

What is claimed is:

1. A method of disinfecting air comprising indirectly heating a porous wick having a top portion which is located in proximity to a source of heat and a bottom portion which is immersed in a liquid disinfecting composition such that the top portion of the wick has a temperature sufficient to generate particles of said disinfecting composition, which particles are then dispersed into air, wherein at least 90% of the particles which are generated have a particle size of no more than 5 microns and wherein the particles are effective to kill air borne bacteria.

2. The method of claim 1 wherein the wick is heated to a temperature in the range of from about 50° to about 120° C.

3. The method of claim 1 wherein the liquid disinfecting composition includes a glycol as an active disinfecting agent.

4. The method of claim 3 wherein the glycol is selected from the group consisting of propylene glycol, dipropylene glycol, triethylene glycol and mixtures thereof.

5. The method of claim 3 wherein the liquid disinfecting composition includes water as a diluent.

6. The method of claim 3 wherein the liquid disinfecting composition comprises from about 5 to 100% of a glycol and from about 95 to 0% water.

7. The method of claim 6 wherein the glycol is dipropylene glycol.

8. The method of claim 7 wherein the liquid disinfecting composition comprises from about 10 to 100% of dipropylene glycol and from about 0 to 90% water.

9. The method of claim 3 wherein the composition also includes less than 15% perfume.

10. The method of claim 3 wherein the composition is essentially perfume free.

* * * * *